(12) United States Patent
Wett

(10) Patent No.: US 10,329,175 B2
(45) Date of Patent: Jun. 25, 2019

(54) METHOD FOR CLARIFICATION OF WASTEWATER

(71) Applicant: Bernhard Wett, Innsbruck (AT)

(72) Inventor: Bernhard Wett, Innsbruck (AT)

( * ) Notice: Subject to any disclaimer, the term of this patent is extended or adjusted under 35 U.S.C. 154(b) by 2 days.

(21) Appl. No.: 15/311,762

(22) PCT Filed: May 28, 2015

(86) PCT No.: PCT/EP2015/061793
§ 371 (c)(1),
(2) Date: Nov. 16, 2016

(87) PCT Pub. No.: WO2015/181270
PCT Pub. Date: Dec. 3, 2015

(65) Prior Publication Data
US 2017/0081222 A1 Mar. 23, 2017

(30) Foreign Application Priority Data

May 28, 2014 (AT) .................................. 50380/2014

(51) Int. Cl.
| | |
|---|---|
| *C02F 3/12* | (2006.01) |
| *C02F 3/30* | (2006.01) |
| *C02F 11/12* | (2019.01) |
| *C02F 1/52* | (2006.01) |
| *C02F 3/04* | (2006.01) |
| *C12P 1/04* | (2006.01) |
| *C02F 11/121* | (2019.01) |
| *C02F 11/14* | (2019.01) |

(52) U.S. Cl.
CPC .................. *C02F 1/52* (2013.01); *C02F 3/04* (2013.01); *C02F 3/1263* (2013.01); *C02F 3/305* (2013.01); *C02F 11/121* (2013.01); *C12P 1/04* (2013.01); *C02F 3/308* (2013.01); *C02F 11/14* (2013.01); *C02F 2209/40* (2013.01); *Y02W 10/15* (2015.05)

(58) Field of Classification Search
CPC .. C02F 1/52; C02F 3/04; C02F 3/1263; C02F 3/305; C02F 11/121; C02F 3/121; C02F 11/12; C12P 1/04; B01D 21/0012; B01D 21/01; B03D 1/26
USPC .................................................. 210/605, 208
See application file for complete search history.

(56) References Cited

U.S. PATENT DOCUMENTS

| | | | |
|---|---|---|---|
| 3,941,698 A | 3/1976 | Weis | |
| 4,487,697 A | 12/1984 | Böhnke et al. | |
| 6,344,143 B1 * | 2/2002 | Ahn | C02F 3/1221 |
| | | | 210/620 |
| 2009/0001016 A1 * | 1/2009 | Lee | C02F 3/1263 |
| | | | 210/605 |

FOREIGN PATENT DOCUMENTS

GB 1563420 3/1980

* cited by examiner

*Primary Examiner* — Claire A Norris
(74) *Attorney, Agent, or Firm* — Dykema Gossett PLLC

(57) ABSTRACT

A method for clarification of wastewater that operates at least two alternating and equal process cycles in two or more clarifiers (1a, 1b), each process cycle consisting of a feed period with concurrent feeding and discharging and a reset period in which excess sludge is removed into a thickener (2a, 2b) and the remaining sludge blanket gets homogenized and pre-settled, wherein at each point of time in at least one clarifier (1a, 1b) the feed period is performed.

18 Claims, 9 Drawing Sheets

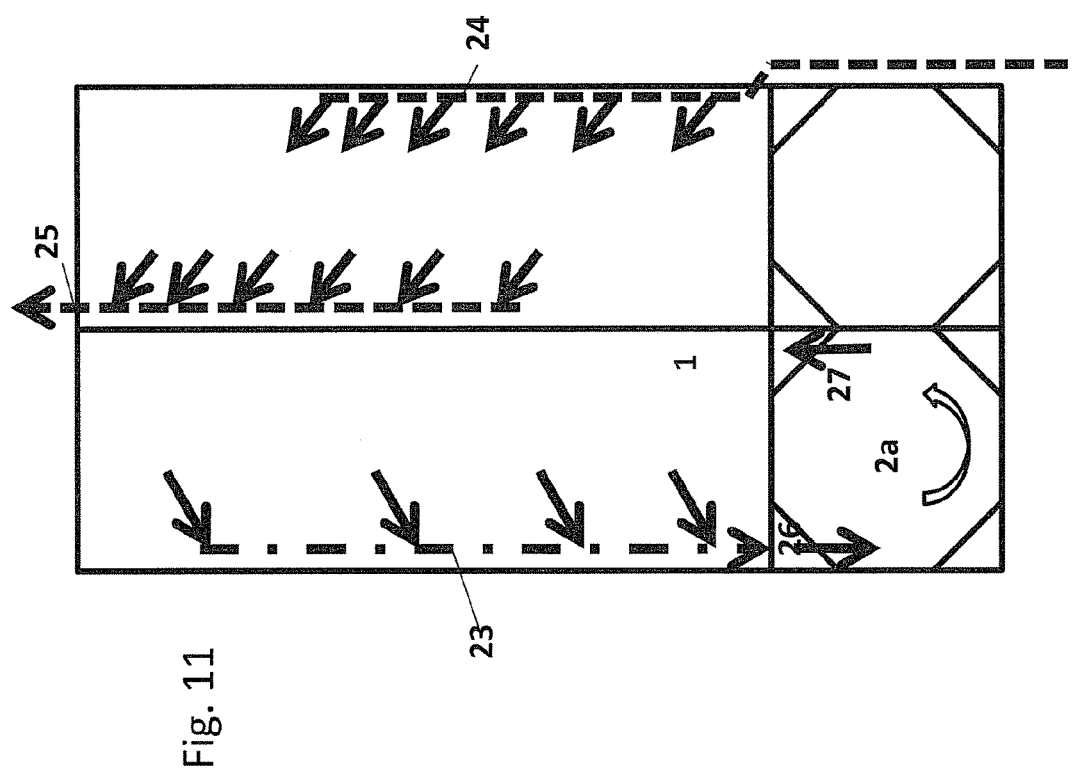

METHOD FOR CLARIFICATION OF WASTEWATER

The invention relates to a method for clarification of wastewater that operates at least two alternating and equal process cycles in two or more clarifiers, each process cycle consisting of a feed period with concurrent feeding and discharging and a reset period in which excess sludge is removed into a thickener and the remaining sludge blanket gets homogenized and pre-settled.

Wastewaters consist of organic material including dilute organic suspensions of colloidal and settleable solids. Efficient and early separation of these solids are important, since the efficient separation allows for maximizing the recovery of energy and resources from the solids and the early separation minimizes its breakdown and degeneration by hydrolytic processes and subsequent wasteful energy liberation without recovery by aerobic oxidation processes. Thus, this energy is preserved and can be further thickened or concentrated and more efficiently recovered using other biological or thermal processes. The method and apparatus for early and efficient separation of suspensions and/or the subsequent thickening/concentration of these suspensions is the subject of this invention.

Several approaches are being used to achieve efficient separation of wastewater organics. The oldest approach is to physically remove only the settleable material using primary clarifiers or sedimentation tanks. These clarifiers that have hydraulic retention times of about 1-2 hours are used to efficiently remove solids in rectangular or circular configurations. The removal of solids occurs using collectors at the bottom of the clarifier that transfer sludge to a small sump with a pump for downstream processing. In some cases, these solids are concentrated in a compaction zone to about 1-2% solids content. Regardless, these solids often need further thickening in a separate downstream process. In some cases gravity based co-thickening of excess-sludge from a downstream activated sludge system pumped into the primary clarifier is reported (e.g. Ross and Crawford, 1985). This method is expected on one hand to improve thickening performance of waste activated sludge and on the other hand removal of organic matter in primary treatment.

A modification of this physical approach for separation is to add chemicals, the earliest example being associated with the use of chemical coagulants and organic flocculants to more efficiently remove finer colloidal non-settleable suspensions through coagulation and subsequent flocculation processes. Efficient coagulation results in 'chemisorption' of organic colloids into material that is amenable to subsequent flocculation. Improved flocculation results in a larger particle aggregate that is then rapidly removed by settling processes. This is often called chemically enhanced primary treatment (CEPT) and is a known and long accepted art for achieving separation. Typical efficiencies of a CEPT can be as high as 70% solids removal and with sufficient coagulants can even exceed these values. However, adding significant amounts of chemicals are wasteful if added continuously and creates significant chemical sludge for downstream processing. Thus an optimum dosage of metal- and polymeraddition can achieve complementary effects for improved solids removal (e.g. Neupane et al., 2008; Cassel et al., 2009).

Another approach developed in the 1970s and 1980s is the A-B process (priority 1979: DE2908134 A1; U.S. Pat. No. 4,487,697) that uses biological means to achieve 'biosorption' of organic material in the 'A' step of the two-step process (Bohnke, 1976; Versprille et al., 1984). This biosorption 'A' step is achieved in a separate reactor/clarifier combination that is maintained at very short solids and hydraulic residence times, the solids residence time typically in the range of 0.25-0.5 days. This biosorption process occurs through a bioflocculation process described to occur using bacterial extracellular polymeric substances (EPS), as the bacteria in sludge change physiological states to form aggreagates when grown at rates slightly slower than their maximum growth rates. This biosorption/bioflocculation results in removal of colloidal and settleable suspensions in the absence of using inorganic chemicals as in the earlier CEPT process. The A step consists of a separated reactor and clarifier, the reactor being operated under aerobic and/or anaerobic or alternating conditions and the clarfier being operated to maximize settlement and concentration of these solids to downstream processes. The solids content of these solids are typically 1% and some amount of recycle (typically 30% of the influent flow-rate) is needed to maintain this activated sludge process. The SRT of the reactor is controlled by aggressive wasting of the concentrated solids from the bottom of the clarifier. The drawback of this process is that its efficiency of solids separation is typically in the 50-60% range and the solids concentration is only about 1%. Furthermore, the bioflocculation process cannot be controlled with the same degree of accuracy as CEPT and process configurations, wastewater temperatures, aeration and shear rates, etc affect and produce variable performance of the biosorption/bioflocculation process. The solids are often further thickened in a downstream process, a process typically not integrated within the separation process of primary clarification. A process integrating separation and storage of compacted particles has been applied for dilute streams in a continuous manner up-stream of primary treatment for grit removal (priority 1976, U.S. Pat. No. 3,941, 698).

A summary of needs is thus presented: 1). It is desirable to integrate the biosorption/bioflocculation step within the physical removals associated with a primary tank or the physical/chemical removals of the CEPT process. The combination will create a more efficient primary tank. This also allows for a process that minimizes footprint, infrastructure, energy and equipment needs. 2). It is also desirable to determine appropriate means to thicken these solids in a near seamless manner in a thickening step such that the separated solids are efficiently concentrated with minimal additional footprint, infrastructure, energy and equipment.

The object of the invention is to minimize the use of footprint, infrastructure, energy and equipment to address the above needs is the subject of this invention.

The present invention relates to a method for clarification of wastewater that operates at least two alternating and equal process cycles in two or more clarifiers, each process cycle consisting of a feed period and a reset period, wherein at each point of time in at least one clarifier the feed period is performed, and wherein the reset period consists of first setting, wasting, aerating and second setting.

The proposed approach is to integrate a biosorption or bioflocculation step within a primary clarifier or a CEPT process, by developing appropriate methods and apparatus that minimize the use of footprint, infrastructure, energy and equipment, to achieve the combined physical/biological or physical/chemical/biological removal in these primary tanks. Additionally, the solids can be further concentrated in a thickener that is collocated adjoining these primary tanks thus co-using equipment and prudently using the available hydraulics for optimally managing the early and efficient removal of solids and the subsequent thickening of these solids. There are many existing primary tanks with excess capacity that can be retrofitted to achieve these different removals integrated in a single tank thus saving footprint, infrastructure, energy and equipment.

The disclosed embodiments include a method and apparatus to develop a frugal approach to improve the separation and/or thickening of organic suspensions, consisting of colloidal and suspended materials within primary tanks using physical, biological and if needed chemical means. The separation is achieved using alternating clarifiers that facilitate alternate intervals of feed, withdrawal, wasting, aeration and settling in a manner to maximize the removal of the organic suspensions while minimizing the use of resources including footprint, infra-structure, energy and equipment. A thickening process is collocated with the settling tank that co-uses the hydraulic changes achieved using the alternating arrangement and shares the equipment and infrastructure associated with the primary tank. This approach results in considerable process intensification while simultaneously reduces the energy and equipment needs associated with separation and thickening of organic suspensions. The alternating approach allows for maximizing treatment by separating the hydraulic steps associated with feeding and withdrawal from the processing steps associated with aeration, settling and wasting. The settler waste pump is connected directly to the collocated thickener and the waste is delivered tangentially. The overflow from the thickener is timed to gravity return to the clarifier through the alternation of levels of clarifier and thickener. The blower/air compressor is coused for both lifting and aeration.

Further the invention relates to an apparatus for clarification of wastewater comprising of at least two clarifiers that are operated in an alternating arrangement, each equipped with influent piping near the bottom of the clarifier; sludge withdrawal near the bottom of the clarifiers; a mixing system using pressurized air; and an effluent piping close to the surface of the clarifier. Such apparatus is apt for conduction the above method.

At least one thickener is provided for further concentration of sludge. Preferably one thickener is provided for each clarifier.

Preferably an inflow pipe is arranged along a side wall of the clarifier at its bottom. In this way inflow can be introduced with very low speed directly into the sludge settled at the bottom. So the sludge blanket helps to retain particles introduced with influent and prevent them from contaminating clear water. Further any introduced organic material will get absorbed by the sludge at the bottom of the clarifier.

BRIEF DESCRIPTION OF THE DRAWINGS

FIG. 11 is a a schematic plan view of another embodiment of the alternating clarifiers.

DETAILED DESCRIPTION OF THE PREFERRED EMBODIMENTS

The disclosed embodiments provide a settler to remove organic suspensions in a wastewater treatment process through an alternating activated adsorption settler. The material removed by this settler includes colloidal and particulate solids. The approach used to remove the solids is to provide only enough aeration time to promote aggregation of solids and removal of colloidal solids through biosorption and bioflocculation processes, but not enough time to cause substantial oxidation of soluble readily degradable organic material or for substantial hydrolysis and breakdown of colloidal solids. The apparatus is designed in a manner to produce a compact design with small footprint and infra-structure (approximately 30-60 min hydraulic residence time) for the associated removals and reduced energy and equipment required for removal of these solids.

Figure 1:
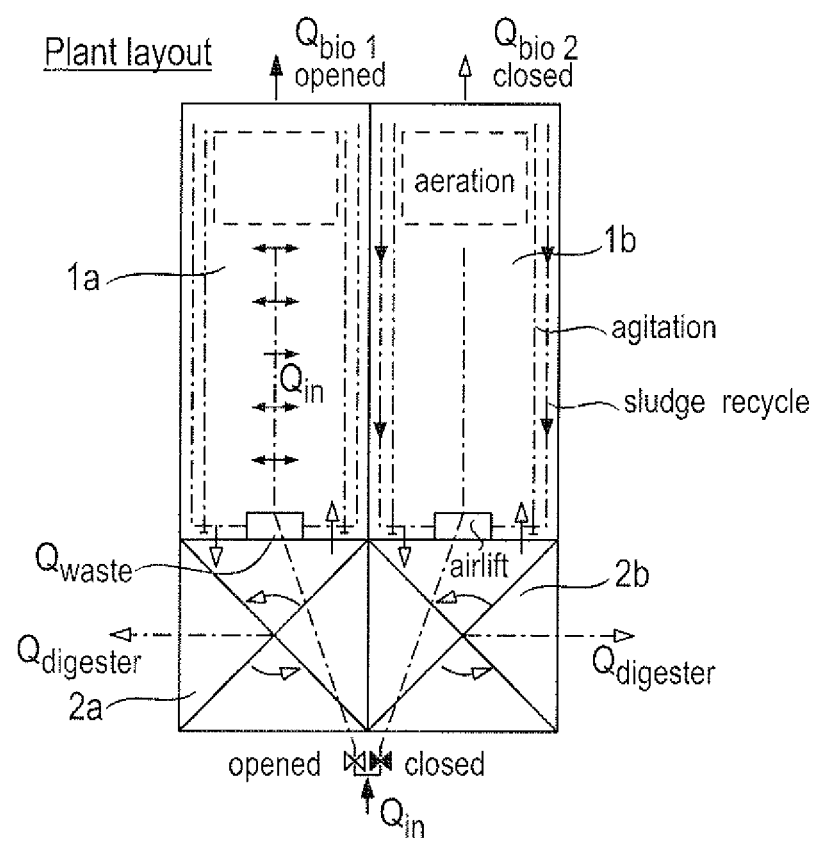
FIG. 1 shows the side-profile view of water levels and operating sequence of the settling and thickening apparatus according to an example embodiment, timed in a sequential manner from a, b, c, d and e.
Figure 2A:
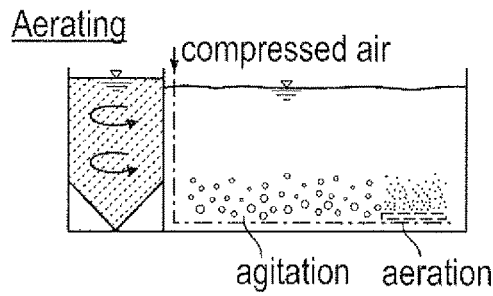
FIGS. 2a-2e provide an example approach of thirty minute phase cycles of two alternating clarifiers. Multiple clarifiers (greater than two) can be used if desired in a sequenced arrangement.

FIG. 1 shows a plan view of the apparatus for clarification of wastewater. It comprises of at least two alternating clarifiers 1a, 1b. The figure shows two clarifiers 1a, 1b, although multiple clarifiers are certainly feasible. Each clarifier 1a, 1b is equipped with influent piping located preferably near the bottom of the clarifier 1a, 1b. FIG. 1 shows the lengthwise distribution of the feed along the bottom of the clarifier 1a, 1b to prevent excessive localized turbulence. FIG. 2a FIG. 2c, respectively show the location of the the feed and sludge withdrawal near the bottom of the clarifiers 1a, 1b. FIG. 1 and FIG. 2d show a mixing system for agitation preferably using pressurized coarse bubble air and an aeration grid preferably with fine bubble diffuser located at the bottom of the clarifier 1a, 1b. FIG. 2a shows an effluent pipe close to the surface of the clarifier 1a, 1b.

FIG. 2c. shows that each clarifier 1a, 1b is hydraulically connected to an optional thickening apparatus in a manner such that the waste solids from the clarifier 1a, 1b are fed into an optional thickener 2a, 2b. The overflow from the thickening apparatus under optimum conditions (such as in FIG. 2c) flows by gravity to the clarifier 1a, 1b. The underflow from the thickener flows to a downstream sludge processing unit, and is controlled by an effluent valve (FIG. 2a).

The levels of the clarifiers 1a, 1b and thickeners are hydraulically arranged to preferably allow for gravity flow of the thickener 2a, 2b overflow back to the clarifier 1a, 1b during the clarifier waste period (FIG. 2c). The extraction of the waste from the clarifier 1a, 1b also shown in FIG. 2c allows for the water level in the clarifier 1a, 1b to drop below the effluent level in a manner that subsequent aeration preferably does not lead to overflow of solids from the clarifier 1a, 1b into the effluent.

FIG. 1 shows the waste from the clarifier 1a, 1b is pumped via a drain pipe adequately separated from the feed pipe to minimize short circuiting and turbulent conditions; and connected to an airlift pump in an alternating sequence preferably using the same source of pressurized air as the air mixing system. Coarse bubble- or fine bubble diffusers are used for transferring air and for mixing/agitating the contents of the clarifier 1a, 1b. The diffuser are located at the bottom of the clarifier 1a, 1b and are shown in the plan view of FIG. 1. The figure discloses as an example the square grid for the fine bubble diffuser and the lengthwise distribution of the coarse bubble diffusers used for agitation.

The settling apparatus uses air where, preferably a configuration of at least two blowers is used with one blower providing air to lift the waste sludge, and subsequently both blowers providing air to the aeration- and air mixing system and a switching valve directing the pressurized air of the same set of blowers to the other clarifier.

FIGS. 2a, 2b, 2c, 2d and 2e describe the phasing of the process cycles. FIG. 3 provides two phased thirty minute time cycle distribution for the different processing steps described in FIGS. 2a, 2b, 2c, 2d and 2e. The clarification and thickening of wastewater operates at least two alternating and equal process cycles; each process cycle consisting of a feed period of total cycle time divided by number of clarifiers. Thus, in the example embodiment of FIG. 3, for two alternating clarifiers 1a, 1b, the feed period is 15 minutes, half of the total cycle time. FIG. 2a shows the first phase where the feed is added to an unmixed settler and with the clarifier feed flow pushing out the supernatant discharge flow during the same period. Preferably during this phase, the thickener underflow is fed to the downstream sludge processing unit.

Figure 2B:
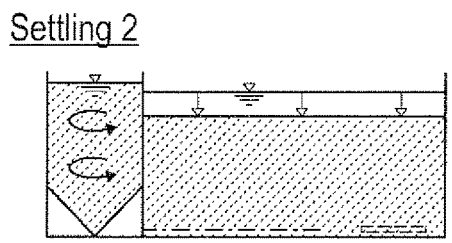
Figure 2C:
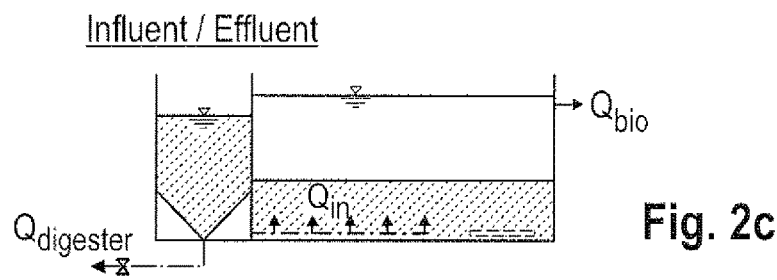
Figure 2D:
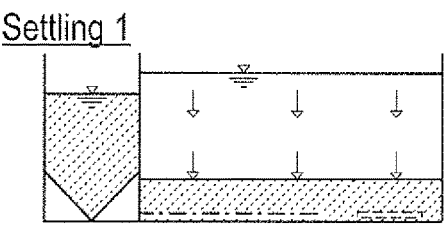
Figure 3:
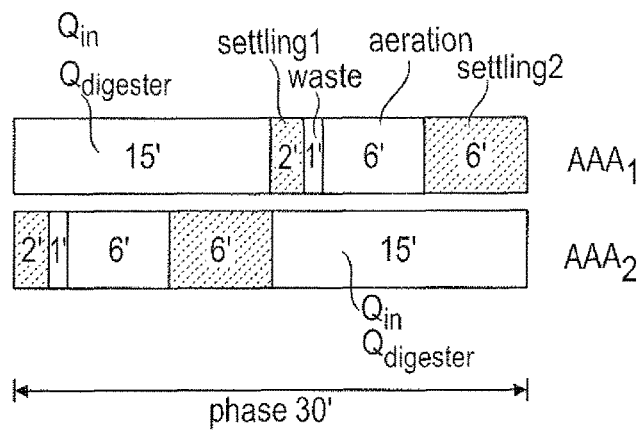
FIG. 3 shows a schematic plan view of the alternating clarifiers. The arrows show the directional movement of flow to the clarifiers and within the clarifier. The plan shows the settlers and the tangential flow thickeners at the bottom of the plan.

Subsequent to the feed phase, the settler continues to concentrate sludge and settle if desired (FIG. 2b).

In the subsequent sludge withdrawal phase shown in FIG. 2c, flow of settled sludge is extracted from the settler and introduced into an optional thickener; with the thickener overflow returned to the clarifier 1a, 1b.

Figure 2E:
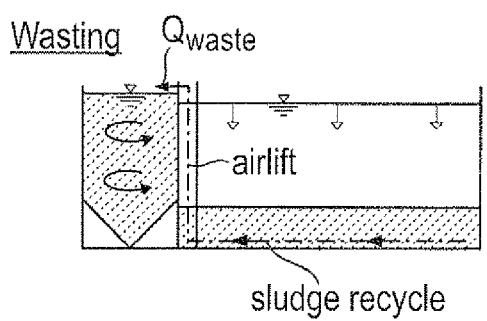

FIG. 2d shows the cycle time for sufficient air-mixing contact period and FIG. 2e shows a settling period before the next feed and discharge period. In this embodiment, the air-mixing period and settling periods are six minutes each as shown in FIG. 3. The air-mixing contact period is used to stir up settled sludge, incorporate floating sludge, and allow for production of extracellular polymeric substances by heterotrophic organisms (especially when growth rates are slightly below the maximum growth rates of the organism) and the subsequent sorption of colloidal and soluble organic matter.

Figure 4:
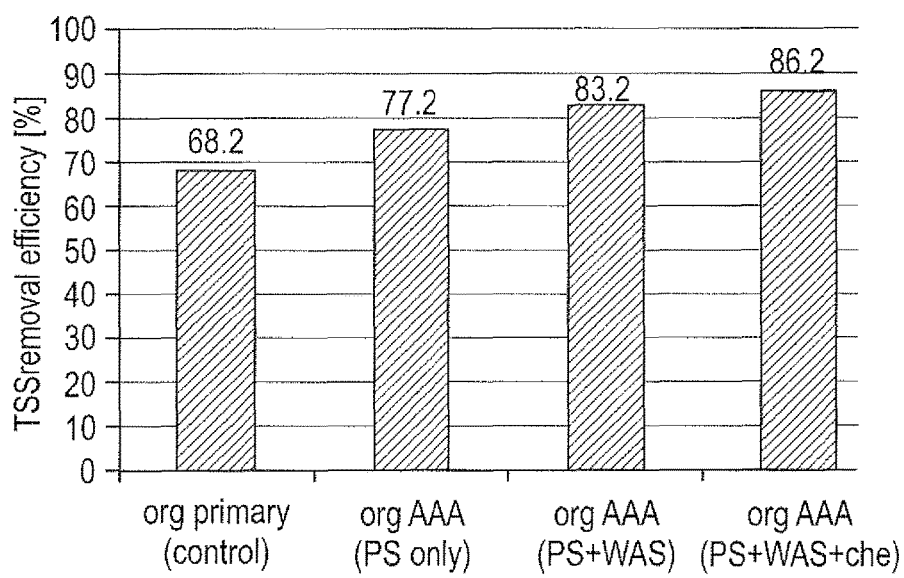
FIG. 4 is a graph showing the average effluent total suspended solids performance of an example settler pilot compared to a primary tank control.
Figure 5:
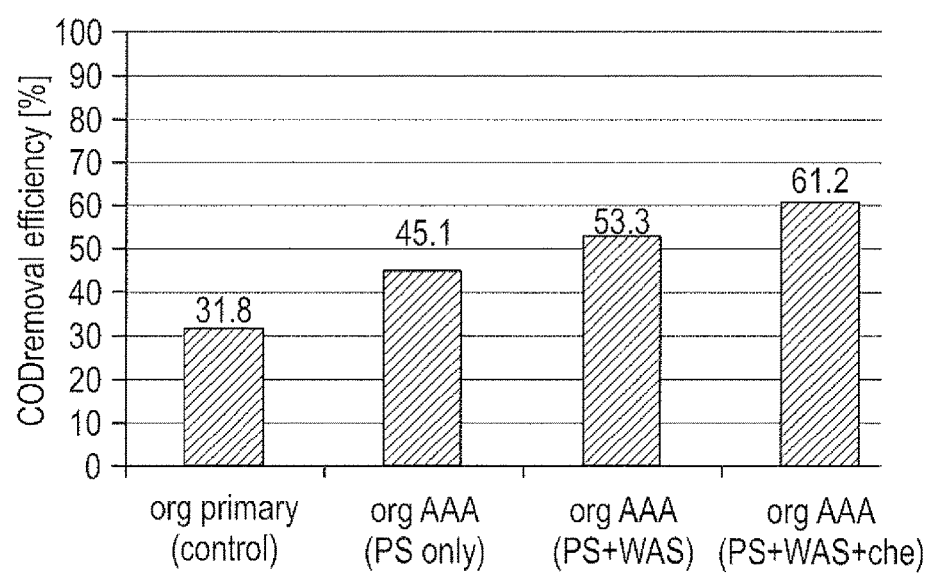
FIG. 5 is a graph showing the average chemical oxygen demand performance of an example settler pilot compared to a primary tank control.

Activated sludge from another downstream or parallel process can be added to the clarifier 1a, 1b to improve removal of organic material. Chemical coagulants (chem) can also be added to the feed before entering the clarifier 1a, 1b. Optionally polymers are added in the clarifier 1a, 1b preferably during the mixing phase to improve removal of organic material. FIG. 4 shows the performance of the AAA settler compared to a primary control for AAA biosorption where only air is added (PS only), for waste activated sludge from another process added (PS+WAS), and for the combined addition of WAS and chemical coagulants (PS+WAS+chem). The figure shows considerable improvements to removal of total suspended solids with each of these successive amended options. FIG. 5 shows the chemical oxygen demand (COD) removal for each of the above amended options. Again, there are considerable improvements of AAA (PS only, PS+WAS and PS+WAS+chem) against a primary control.

Figure 6:
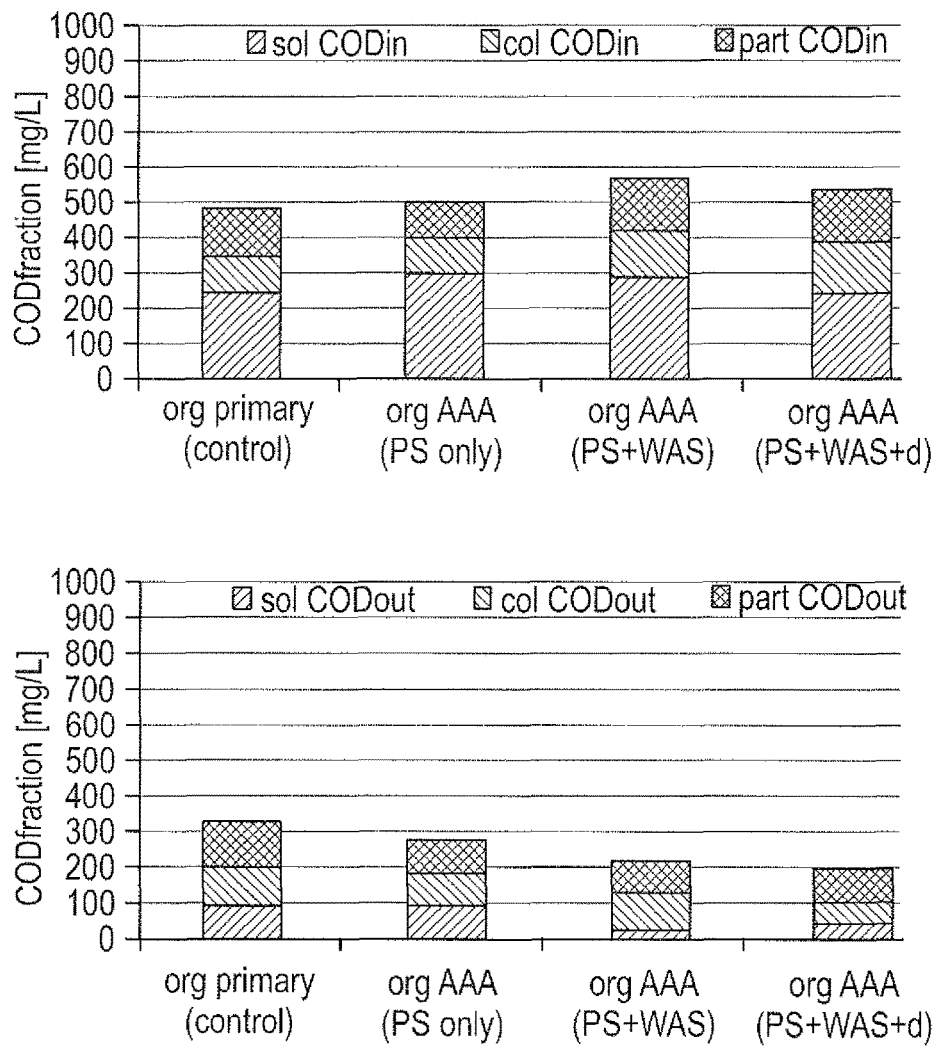
FIG. 6 is a graph showing the fractionation of the influent and effluent chemical oxygen demand for an example settler pilot compared to a primary tank control.

FIG. 6 shows the fractions of particulate (settleable solids), colloids, and soluble material in the influent and effluent of a AAA settler against a primary control. Smaller concentrations of particulate and colloidal fractions in the effluent are desired. The AAA settler (PS only), the WAS amendment (PS+WAS), and chemical amendments (PS+WAS+chem) consistently have lower particulate and colloidal COD compared to the control suggesting superior process performance for efficient removal of these organic suspensions. In FIG. 6, the soluble COD is somewhat removed by the AAA settler options, but much is still available for downstream processes (such as for denitrification or biological phosphorus removal). Thus the AAA settler show remarkable efficiency for removal of particulates and colloids using biosorption (and optional chemisorption) and bioflocculation (and optional chemical flocculation), while allowing the soluble fraction to pass through.

Figure 7:
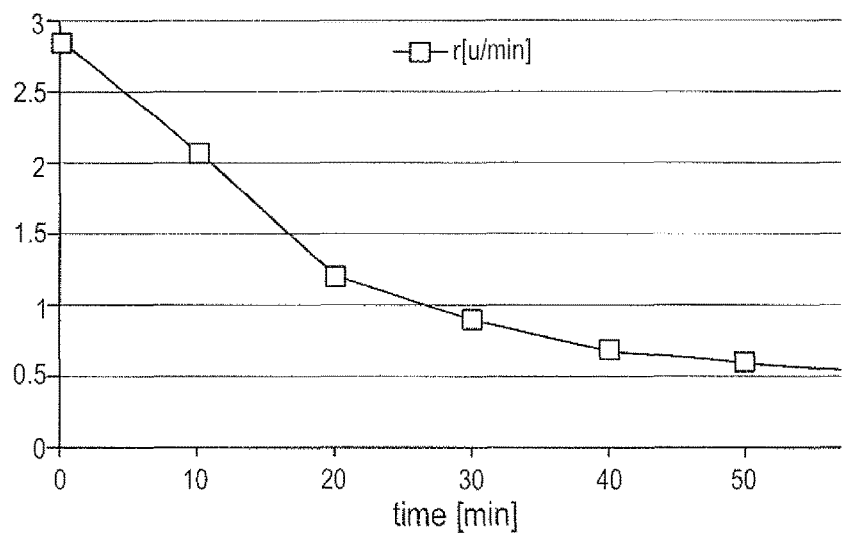
FIG. 7 is a graph showing an example velocity profile of the tangential flow thickener in revolutions per minute.
Figure 8:
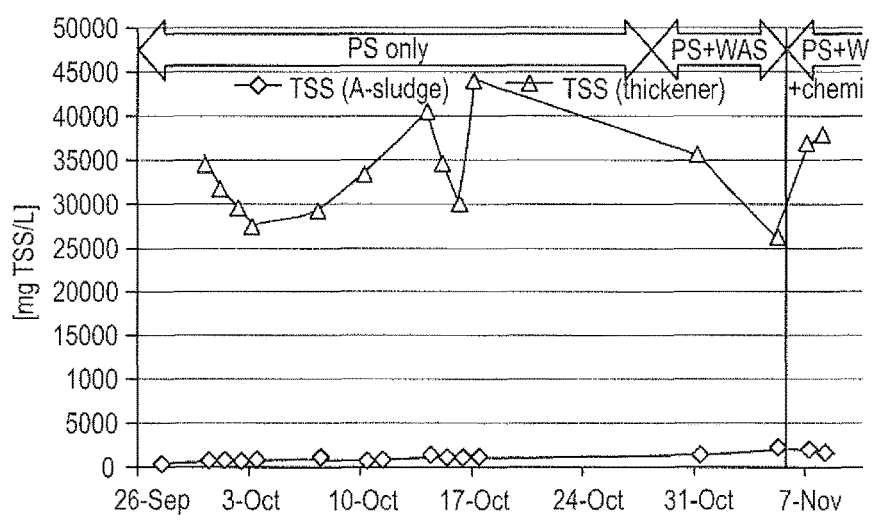
FIG. 8 is a graph showing an example thickening performance of a tangential flow thickener.

The waste from the clarifier 1a, 1b is fed tangentially to the thickener 2a, 2b to induce a gentle circular current to improve thickening performance. FIG. 7 shows the tangential rpm during the introduction of the feed and the retained momentum even after the feed addition is stopped (roughly after 15 minutes). The ability of the thickener to maintain this momentum substantially reduces 'rat-holing' and short circuiting of thickener supernatant through the thickened blanket. This slow flow also allows for improved and rapid thickening. FIG. 8 shows the thickening performance for the AAA sludges (PS only, PS+WAS, PS+WAS+chemicals). The thickener is able to thicken to solids concentrations exceeding 30,000 mg/L (3%) with only a shallow design permitted for the pilot demonstration. Deeper and larger clarifiers 1a, 1b could allow for rapid thickening in excess of 5% solids.

Figure 9:
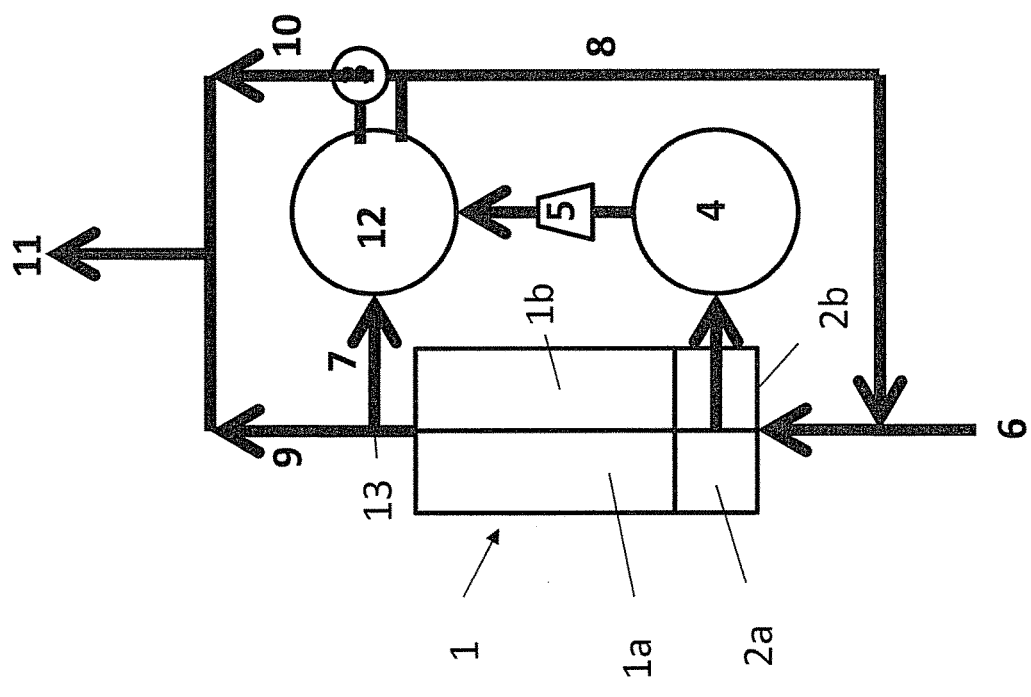
FIG. 9 is a flow-scheme showing a possible integration of the method of the invention into an overall clarification process.

Settling- and biosorption processes are usually applied for removal of organics (mainly carbon-compounds) and not for nitrogen removal. In order to enhance nitrogen removal the following solution shown in FIG. 9 has been developed:

The unit consisting of two clarifiers 1a, 1b and thickeners 2a, 2b as described above is referred to in total as AAA-settler 1. This AAA-settler 1 is designed in a way that maximum capacity equals two times maximum dry water flow (2*Qdw).

At 13 the discharge flow of the AAA-settler 1 is divided into a first effluent 9 and a feed 7 for a trickling filter 12. This feed 7 should equal at least maximum dry weather flow Qdw. In the trickling filter 12 almost all the ammonia will be oxidized to NOx and the nitrate containing recycle stream 8 containing nitrate and the waste-sludge of the trickling filter will be fed mainly to the influent of the AAA-settler 1.

The trickling filter 12 is also connected to a digester 4 and a dewatering unit 5. The captured organics will be fed from the integrated thickeners 2a, 2b to the digester 4 and the dewatering liquors can be fed from the dewatering unit 5 directly to the trickling filter 12 for ammonia removal.

The recycle stream 8 is limited in order to keep flow through the AAA-settler 1 near to the maximum value of two times maximum dry water flow (2*Qdw), but not to exceed this value. The excess flow of separation unit 3 is separated as a second effluent 10. Together with first effluent 9 it makes the effluent 11.

The nitrate will be introduced together with the carbon of the raw sewage into the sludge blanket of the AAA-settler. This configuration will allow high denitrification rates and will also significantly contribute to the performance of organics-removal since electron acceptors will be available not only during aeration periods but also during non-aerated periods. Odor mitigation represents an additional benefit of nitrate recycling since nitrate increases the redox-potential in the AAA-reactor minimizing anaerobic degradation processes.

The quality of the effluent 11 can be optimized depending on the portion of AAA-effluent 9 with minimum nitrate and the portion of trickling filter effluent second effluent 10 with minimum ammonia send to the effluent 11. Alternatively in a simplified flow scheme all the trickling filter effluent can be recycled directly to the AAA-settler 1 without installation of a separation unit 3.

Figure 10:
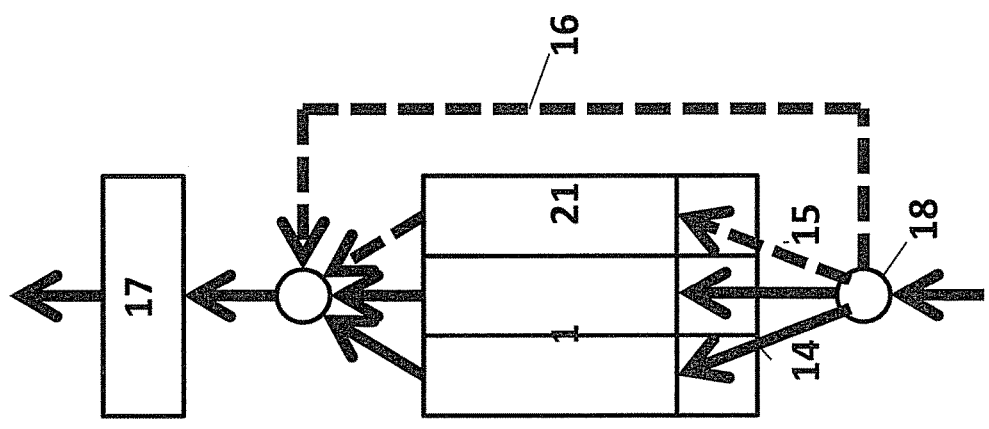
FIG. 10 is another flow-scheme showing an alternative integration of the method of the invention.

Another approach to handle different inflow rates in order to optimize volume and foot-print of the organics removal system is shown in FIG. 10. In this case, the AAA-settler 1 should be designed for dry-weather-flow only. Excess influent-flow can be directed to a conventional primary settler 21 in parallel to the AAA-settler 1 to handle following flow-scenarios:

Dry-weather flow: To keep the primary treatment system operative also at dry-weather days a minimum influent-flow to the primary tank should be provided or the influent flow 14 to the AAA-settler 1 should be set to a maximum rate shaving off the dry-weather-flow peaks and feeding this differential 15 to the primary treatment.

Wet-weather flow: All influent flow in excess to the design-flow of the AAA-settler 1 is fed to the primary treatment via bypass 16. Flow distribution is controlled by an influent valve 18 and a flow-meter.

Redundancy and maintenance: In case the AAA-settler needs to be taken off-line, all the influent flow is fed to the primary settler. In case the primary settler needs to be taken off-line, the design-flow is fed to the AAA-settler and the excess-flow is by-passed 16 to the down-stream biological treatment 17.

The AAA-settler is typically designed for ca. 2 hours hydraulic retention time at dry-weather flow and the primary settler is designed for ca. 0.5 hours hydraulic retention time at wet-weather flow. This means at a peaking factor of ca. 2.5 the volume requirement for the primary settler will be about half of the reactor volume of the AAA-settler 1.

FIG. 11 Similar to primary settlers the AAA-settler 1 preferably shows a stretched geometry with the width of the reactors 1a, 1b similar to the width of the integrated thickeners 2a, 2b. This embodiment provides the flow-schemes with the left-hand-side reactor in sludge recycle phase while the right-hand-side reactor is in fill-and draw mode. At least one drain-pipe 23 for sludge recycling is needed (e.g. installed along the length-side wall at the bottom) apart from the influent pipe 24 (e.g. installed along the opposite length-side wall at the bottom). The air-lift 26 (e.g. installed in the corner-space between thickener octagon and sidewall) sucks the settled sludge layer via the connected drain-pipe and pushed the waste-sludge diagonally at the water surface into the thickener. Excess-liquor from the thickener can be returned via the other corner-space 27 to the reactor. The influent flow is introduced into the sludge blanket via lateral openings of the influent pipe 24. Along the flow-path to the submerged effluent pipe 25 (e.g. installed near the water surface on the length-side opposite the influent pipe) the solids settle out and organics get adsorbed by the biomass in the sludge blanket.

The invention is not limited to the structures, methods and instrumentalities described above and shown in the drawings. The invention is defined by the claims set forth below.

The invention claimed is:

1. A method for clarification of wastewater that operates at least two alternating and equal process cycles in two or more clarifiers, each process cycle consisting of a feed period with concurrent feeding and discharging and a reset period in which excess sludge is removed into a thickener and a remaining sludge blanket gets homogenized and pre-settled, wherein at least one of the two or more clarifiers is in the feed period at each point of time.

2. The method of claim 1, wherein the duration of the feed period equals a total cycle time divided by number of clarifiers.

3. The method of claim 2, wherein the rest period includes the step of wasting, the wasting step includes airlifting sludge from the at least one of the two or more clarifiers into the thickener.

4. The method of claim 3, wherein sludge is transferred from the first clarifier to the thickener allocated to the first clarifier and that sludge is removed from the thickener during the feed period in the first clarifier allocated to that thickener, and sludge is transferred from a second clarifier to a second thickener allocated to the second clarifier and that sludge is removed from the second thickener during a feed period in the second clarifier allocated to the second thickener.

5. The method of claim 4, wherein in the thickener a circular flow is induced by tangential introduction of the sludge.

6. The method of claim 5, further including a clarifier waste period wherein the levels of the clarifiers and thickeners are hydraulically arranged to allow for gravity flow of the thickener overflow back to the clarifier; and the extraction of the sludge allows for the water level in the clarifier to drop below an effluent level in a manner that subsequent aeration does not lead to overflow of solids from the clarifier into the effluent.

7. The method of claim 6, wherein during the feed period wastewater is conducted into a bottom region of the clarifier into a sludge blanket.

8. The method of claim 7, wherein during the feed period the feed flow pushes out a remaining supernatant discharge flow while maintaining almost constant water level.

9. The method of claim 8, wherein the feed period and the reset period are of equal length, and the two or more clarifiers are of even quantities.

10. The method of claim 9, wherein activated sludge is added to the clarifier to improve removal of organic material.

11. The method of claim 10, wherein a coagulant is added to the feed before entering the clarifier and optionally polymers are added in the clarifier.

12. The method of claim 11, wherein aerating is used to stir up settled sludge, incorporate floating sludge, and allow for production of extracellular polymeric substances by heterotrophic organisms and the subsequent sorption of colloidal and soluble organic matter.

13. The method of claim 12, wherein biological phosphorus uptake is enhanced in the clarifier by adding biomass from a downstream biological treatment unit or by recycling biomass from the allocated thickener.

14. The method of claim 13, wherein stored Polyhydroxy Alkanoates (PHA) from accumulated organisms is extracted from the underflow of the thickener.

15. The method of claim 14, wherein at least a part of the effluent of the clarifiers is treated in a trickling filter and fed back to the clarifiers.

16. The method of claim 15, wherein a digester is provided which is fed by organic material from the thickeners and which discharges into the trickling filter, via a dewatering unit.

17. The method of claim 16, wherein a part of an influent flow to the clarifiers is bypassed to a parallel primary settler or directly to the downstream biological treatment.

18. The method of claim 2, wherein the reset period consists of first settling, wasting, aerating and second settling.

* * * * *